(12) United States Patent
Cakir et al.

(10) Patent No.: US 8,691,778 B2
(45) Date of Patent: *Apr. 8, 2014

(54) FLURBIPROFEN AND MUSCLE RELAXANT GEL COMBINATIONS THEREOF

(75) Inventors: Fatih Cakir, Istanbul (TR); Ali Turkyilmaz, Istanbul (TR); Umit Cifter, Istanbul (TR)

(73) Assignee: Sanovel Ilac Sanayi ve Ticaret Anonim Sirketi (TR)

( * ) Notice: Subject to any disclaimer, the term of this patent is extended or adjusted under 35 U.S.C. 154(b) by 164 days.

This patent is subject to a terminal disclaimer.

(21) Appl. No.: 12/885,602

(22) Filed: Sep. 20, 2010

(65) Prior Publication Data

US 2011/0071098 A1 Mar. 24, 2011

(30) Foreign Application Priority Data

Sep. 18, 2009 (TR) .................................. 200907179

(51) Int. Cl.
- *A01N 43/04* (2006.01)
- *A61K 31/70* (2006.01)
- *A01N 37/10* (2006.01)
- *A61K 31/19* (2006.01)

(52) U.S. Cl.
USPC ............................................ 514/33; 514/570

(58) Field of Classification Search
None
See application file for complete search history.

(56) References Cited

U.S. PATENT DOCUMENTS

| 4,393,076 A * | 7/1983 | Noda et al. ..................... 424/499 |
| 4,473,584 A * | 9/1984 | Heckler ........................ 514/570 |
| 5,807,568 A | 9/1998 | Cody et al. |

FOREIGN PATENT DOCUMENTS

| EP | 1992333 A1 | 11/2008 |
| FR | 2725134 A1 | 4/1996 |
| WO | WO9523596 | 9/1995 |
| WO | WO9641635 | 12/1996 |
| WO | WO9852545 | 11/1998 |
| WO | WO2007129162 A2 | 11/2007 |

OTHER PUBLICATIONS

Rasheed. Studies of Cyclooxygenase-1(COX-1) and cyclooxygenase-2 (COX-2) Inhibitors with Analgesic, Anti-inflammatory and Anti-platelet, Thesis, 2003, abstract.*
Morimoto, et al., "Effect of I-Menthol-Ethanol-Water System on the Systemic Absorption of Flurbibrofen . . ." Bio. & Pharma. Bulletin of Japan, vol. 23, No. 10, pp. 1254-1257, 2000.
Loganathan, et al., "The Effects of Polymers and Permeation Enhancers on Releases of Flurbiprofen . . . " Indian Journal of Pharma., vol. 63, No. 3, pp. 200-204, May 1, 2010.
European (IB) Search Report for TR200907179 dated Apr. 7, 2010 (8 pages).

* cited by examiner

*Primary Examiner* — Layla Bland
(74) *Attorney, Agent, or Firm* — Hiscock & Barclay, LLP

(57) ABSTRACT

A topical pharmaceutical gel includes flurbiprofen or a pharmaceutically acceptable salt of flurbiprofen, thiocolchicoside or a pharmaceutically acceptable salt of thiocolchicoside, and menthol. Pharmaceutical combinations of flurbiprofen, thiocolchicoside, and menthol in the form of topical gels with anti-inflammatory, analgesic, and myorelaxant activities are described.

12 Claims, No Drawings

FLURBIPROFEN AND MUSCLE RELAXANT GEL COMBINATIONS THEREOF

CROSS REFERENCE TO RELATED APPLICATIONS

This application is based upon Turkish Patent Application No. TR200907179, filed Sep. 18, 2009, under relevant sections of 35 USC §119, the entire contents of this application being incorporated by reference herein.

TECHNICAL FIELD OF THE INVENTION

The present invention relates to novel pharmaceutical combinations of flurbiprofen or a pharmaceutically acceptable salt thereof, and thiocolchicoside or a pharmaceutically acceptable salt thereof, as well as of menthol, with anti-inflammatory, analgesic, and myorelaxant activities.

The present invention more particularly relates to pharmaceutical combinations of flurbiprofen, thiocolchicoside, and menthol in the form of topical gels with anti-inflammatory, analgesic, and myorelaxant activities. The rate of percutaneous penetration of said combination is enhanced with the auxiliaries it contains.

BACKGROUND OF THE INVENTION

Flurbiprofen is a propionic acid derivative, also known as NSAID (non-steroidal anti-inflammatory drug), with the analgesic and anti-inflammatory activities it possesses. Its chemical structure is illustrated with Formula 1 given below.

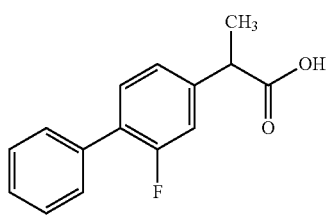

Formula 1

Flurbiprofen is used for alleviating pain in muscle-skeleton system and joint disorders such as ankylosing spondylitis, osteoarthritis, and rheumatoid arthritis, in soft tissue injuries such as sprains and strains, in postoperative cases, and in painful and severe menstruation and migraine. Flurbiprofen is further used as a lozenge in symptomatic amelioration of sore throats.

Flurbiprofen sodium is used for preventing intraoperative miosis, as well as in ophthalmic veins for controlling inflammation of the eye's anterior layer following surgery. Flurbiprofen is administered via intravenous injection against severe pains in some countries.

Thiocolchicoside is a myorelaxant, with the following structure illustrated in Formula 2.

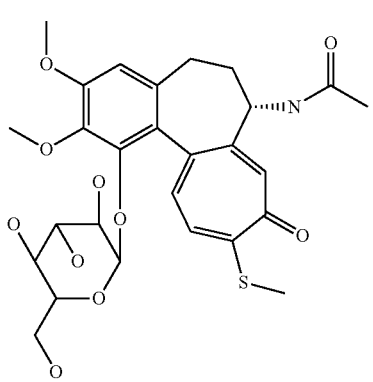

Formula 2

This natural glycoside muscle relaxant has anti-inflammatory, analgesic effects. Thiocolchicoside exerts the myorelaxant effect by activating GABA and glycine receptors at the spinal level.

Muscle relaxants also reduce the muscle tonus and are used in treating muscle spasms and contractures. Muscle spasm is one of the main factors held responsible for chronic pains; in addition to rheumatic inflammatory and degenerative orthopedic pathologies, it defines various pathologies of the locomotor system as well; when it effects the joints, it does not cause pain only, but it leads to stiffness that reduces the mobility and flexibility of joints at the affected site.

Muscle relaxants are used in neuromuscular and muscle-skeleton system injuries. There are two main type of muscle relaxants: centrally-acting muscle relaxants and directly-acting muscle relaxants.

Centrally-acting muscle relaxants typically act on the central nervous system (CNS) in a selective manner and are primarily used for alleviating painful muscle spasms and the strains occurring during muscle-skeleton system and neuromuscular damages. The action mechanisms thereof are associated with the causes of CNS-suppressing activities.

Accordingly, muscle relaxants and antispasmodic molecules constitute a subject matter which is still clinically significant.

Recently, it has been reported that the activity of thiocolchicoside was based on its capability of interacting with strychnine-sensitive glycine receptors, and therefore compounds with glycinomimetic activities have been introduced for use in rheumatologic-orthopedic fields as muscle relaxants.

Researching the patent literature may result in various patents, which relate to flurbiprofen and thiocolchicoside.

The application WO 98/52545 relates to pharmaceutical compositions comprising a combination of flurbiprofen with a therapeutically effective amount of one or more active ingredients selected from an antihistamine, a cough suppressant, a decongestant, an expectorant, a muscle relaxant, a centrally acting analgesic, a local anesthetic, an antibacterial compound, an antiviral compound, an antibiotic compound, an antifungal compound, minerals and vitamins and/or a burn-masking amount of an agent which has a warming effect on the mucosa of the throat.

The U.S. Pat. No. 5,807,568 discloses a topically-administered formulation comprising flurbiprofen as the active agent.

The patent WO9523596 discloses a flurbiprofen solvent in a C2-4 alcohol.

The patent FR 2 725 134 discloses a novel pharmaceutical composition containing ibuprofen or a pharmaceutically acceptable salt thereof and thiocolchicoside or a pharmaceutically acceptable salt thereof in a proportion ranging from 1:50 to 1:200. According to that invention, said pharmaceutical composition is useful in treating painful muscle syndromes and more specifically in treating lumbagos.

The patent EP 0 837 684 discloses pharmaceutical compositions containing, in solid form, a diclofenac salt and thiocolchicoside, combined with at least one pharmaceutically acceptable carrier, for use in therapy.

There has not been developed any pharmaceutical gel until today, which comprises a combination of thiocolchicoside, flurbiprofen, and menthol. Even if muscle relaxants and nonsteroidal inflammatory drugs have been used together in practice, this fact requires the patients to carry more than one drugs and causes application-related difficulties.

The use of flurbiprofen in treating local pains and inflammations may cause a problem especially for those who have gastrointestinal system disorders. It is possible to develop various locally-administrable topical forms of flurbiprofen, in order to avoid the systemic side-effects thereof. The skin absorption rate of the relevant product to be used in topical applications, however, is quite significant. Enhancing the absorption rate both provides ease of application and increases the molecule's efficiency.

Even if there is not any problem associated with the absorption of thiocolchicoside, which is the other active ingredient used in the formulation, the requirement is obvious to increase the rate of absorption particularly during acute situations.

Particularly in acute disorders, there arises the need of enhancing the absorption rate at the site of administration.

In instances during which local pains associated with injuries in sportive events are to be urgently alleviated, it becomes necessary to apply local anesthesia to the relevant site.

In result, the aforesaid drawbacks require a novelty in the art of pharmaceutical combinations with anti-inflammatory, analgesic, and myorelaxant activities.

SUMMARY AND DESCRIPTION OF THE INVENTION

The present invention relates to an easily applicable flurbiprofen, thiocolchicoside, and menthol combination, eliminating all aforesaid problems and brining additional advantages to the relevant prior art.

Accordingly, the main object of the present invention is to obtain a stable gel formulation of flurbiprofen, thiocolchicoside, and menthol with anti-inflammatory, analgesic, and myorelaxant activities.

Another object of the present invention is to increase the rate of percutaneous penetration, thereby shortening the time period in which the active agents exert their effect.

A further object of the present invention is to obtain a formulation with local anesthetic effect, with the menthol used in said combination stimulating the receptors by which the cold sensation is perceived.

Accordingly, a topical pharmaceutical gel has been developed to achieve all objects referred to above and to emerge from the following detailed description.

In a preferred embodiment according to the present invention, said novelty is realized with flurbiprofen or a pharmaceutically acceptable salt thereof, thiocolchicoside or a pharmaceutically acceptable salt thereof, together with menthol.

The amount of menthol makes up 0.05 to 10%, preferably 0.1 to 5%, and more preferably 0.25 to 3% of the total weight of composition.

According to a preferred embodiment, the present invention contains polysorbate as a percutaneous penetration enhancer. The amount of polysorbate is 0.05 to 5%, preferably 0.10 to 4%, and more preferably 0.25 to 3% of the total weight of composition.

According to a preferred embodiment, the present invention contains ethyl alcohol as a percutaneous penetration enhancer and as a solvent. The amount of ethyl alcohol makes up 0.05 to 40%, preferably 0.10 to 25%, and more preferably 0.25 to 20% of the total weight of composition.

In a further preferred embodiment according to the present invention, at least one or a mixture of carbomer and/or triethanolamine is used as a viscosity and gellifying enhancer.

In another preferred embodiment according to the present invention, polyethylene glycol is used as a solvent.

In a further preferred embodiment according to the present invention, the amount of flurbiprofen makes up 0.10 to 10%, preferably 0.10 to 8%, and more preferably 0.25 to 6% of the total weight of composition, whereas the amount of thiocolchicoside makes up 0.05 to 7%, preferably 0.10 to 6%, and more preferably 0.15 to 5% of the total weight of composition.

Another aspect of the present invention provides a method for preparing the pharmaceutical gel according to the present invention, this method comprising the steps of a. adding carbomer into water and swelling this mixture under stirring so as to yield the first mixture, b. adding and dissolving flurbiprofen into alcohol in a separate container and then adding menthol previously dissolved in alcohol into this mixture so as to give the second mixture, c. dissolving thiocolchicoside in polyethylene glycol and adding this mixture into the second mixture, then adding polysorbate into the resultant mixture so as to yield the third mixture, d. adding the third mixture into the first mixture under stirring; and e. adding triethanolamine into the resultant final mixture, then gellifying and stirring this mixture with adding water into it.

In a further preferred embodiment of the present invention, said pharmaceutical gel contains the following ingredients only:

| | |
|---|---|
| a. flurbiprofen | at 0.10 to 10% by weight |
| b. thiocolchicoside | at 0.10 to 5% by weight |
| c. menthol | at 0.05 to 10% by weight |
| d. carbomer | at 0.10 to 4% by weight |
| e. polyethylene glycol | at 2 to 50% by weight |
| f. triethanolamine | at 0.10 to 5% by weight |
| g. polysorbate | at 0.10 to 15% by weight |
| h. ethyl alcohol | at 2 to 50% by weight |
| i. purified water | at 30 to 60% by weight. |

DETAILED DESCRIPTION OF THE INVENTION

Example

| Content | amount (%) (w/w) |
|---|---|
| Flurbiprofen | 5.0 |
| Thiocolchicoside | 0.25 |
| Menthol | 2.50 |
| Carbomer 940 | 1.50 |
| Polyethylene glycol 400 | 10.00 |
| Triethanolamine | 0.15 |
| Polysorbate 80 | 2.0 |
| Ethyl alcohol | 20.0 |
| Purified water | 58.60 |

Carbomer 940 is added into water under stirring and the mixture is swollen by keeping it stirred. Thus, the first mixture is obtained. Flurbiprofen is dissolved in a separate container and menthol, previously dissolved in alcohol, is added into this mixture. Thus, the second mixture is obtained. Then thiocolchicoside is dissolved in polyethylene glycol and added into the second mixture, then polysorbate is added therein so as to yield the third mixture. The third mixture obtained is added into the first mixture under stirring. Into the resultant final mixture is added triethanolamine, then it is brought into a gelled state and the procedure is completed with adding water therein.

With the formulation made according to the present invention, a novel formulation with anti-inflammatory, analgesic, and myorelaxant activities is obtained surprisingly, which is rapidly absorbed and gives local anesthetic effect.

The pharmaceutical compositions according to the present invention may also comprise one or more pharmaceutically acceptable excipients. Such proper pharmaceutically acceptable excipients include, but are not restricted to gel forming agents, viscosity enhancers, surface active agents, penetration enhancers, chelating agents, preservatives, antioxidants, odor masking agents, solvents etc. and mixtures thereof.

Menthol used in the formulation both increases percutaneous penetration and gives anesthetic effect at the side of administration as a result of stimulating the receptors by which cold sensation is perceived. This effect also brings about mental and psychological relief on the subject. Any unwanted odors which probably occur are also eliminated in this way, depending on the percentage of which is 0.05 to 10%, preferably 0.1 to 5%, and more preferably 0.25 to 3% of the total weight of composition.

Polysorbate 80, used as the surface active agent, as well as one or a mixture of dimethyl sulfoxide, ethyl alcohol, and/or polysorbate, used as the percutaneous penetration enhancer raise up the rate of absorption of the composition, thereby substantially shortening the therapy process. The amount of said percutaneous penetration enhancer makes up 0.05 to 5%, preferably 0.1 to 4%, and more preferably 0.25 to 3% of the total weight of composition. Ethyl alcohol is also utilized as a microbiological preservative.

At least one or a mixture of carbomer and/or triethanolamine is used as the viscosity and gellifying enhancer.

Accordingly, the present invention provides topical pharmaceutical combinations, comprising flurbiprofen or a pharmaceutically acceptable salt thereof, thiocolchicoside or a pharmaceutically acceptable salt thereof, and specific amount of menthol, in the form of suspensions, ointments, cream, or gels with anti-inflammatory, analgesic, and myorelaxant activities.

For this reason, the present invention may be used for treating osteoarthritis, pain associated with tissue trauma emerging following osteoarthritis surgery, psoriatic arthritis, rheumatoid arthritis, myalgia, bone pain, pain, arthralgia, muscle spasms, soft tissue traumas, lumbago, back pain, sciatica, ankylosing spondylitis, and torticollis.

Proper gel forming agents include, but are not restricted to carbomer 940, carbomer 941, gelatin, carbomer copolymer, aluminum monostearat, dextrin, magnesium aluminum silicate, silicon dioxide, sodium alginate, triethanolamine, polyvinyl alcohol, pectin, methylcellulose, hydroxypropyl cellulose and mixtures thereof. The most preferred gel forming agents are carbomer 940 and triethanolamine.

Convenient surface active agents and percutaneous penetration enhancers include, but are not restricted to ethanol, menthol, dimethyl sulfoxide, diethanolamine, glyceryl monostearate, oleic acid, sodium lauril sulfate, propylene glycol, polyethylene glycol succinate, polysorbate 20, polysorbate 40, polysorbate 60, polysorbate 80, etc. and mixtures thereof. The most preferred among those are one or a mixture of polysorbate 80, ethanol, and/or menthol.

The present invention is hereby disclosed by referring to an exemplary embodiment hereinabove. Whilst this exemplary embodiment does not restrict the object of the present invention, the latter must be assessed under the light of the foregoing detailed description.

The invention claimed is:

1. A topical pharmaceutical gel comprising:
   flurbiprofen or a pharmaceutically acceptable salt of flurbiprofen, wherein the amount of flurbiprofen makes up 0.10 to 10% of the total weight of composition;
   thiocolchicoside or a pharmaceutically acceptable salt of thiocolchicoside, wherein the amount of thiocolchicoside makes up 0.05 to 7% of the total weight of composition;
   menthol, wherein the amount of menthol is 0.05 to 10% of the total weight of composition;
   ethyl alcohol, wherein the amount of ethyl alcohol makes up 0.25 to 20% of the total weight of composition; and
   carbomer.

2. The pharmaceutical gel according to claim 1, wherein the amount of menthol is 0.1 to 5% of the total weight of composition.

3. The pharmaceutical gel according to claim 1, wherein the amount of menthol is 0.25 to 3% of the total weight of composition.

4. The pharmaceutical gel according to claim 1, further comprising polysorbate as a percutaneous penetration enhancer.

5. The pharmaceutical gel according to claim 4, wherein the amount of polysorbate is 0.05 to 5% of the total weight of composition.

6. The pharmaceutical gel according to claim 4, wherein the amount of polysorbate is 0.10 to 4% of the total weight of composition.

7. The pharmaceutical gel according to claim 4, wherein the amount of polysorbate is 0.25 to 3% of the total weight of composition.

8. The pharmaceutical gel according to claim 1, wherein the inclusion of ethyl alcohol provides same as a percutaneous penetration enhancer and solvent to the gel.

9. The pharmaceutical gel according to claim 1, further comprising triethanolamine.

10. The pharmaceutical gel according to claim 1, further comprising polyethylene glycol as a solvent.

11. The pharmaceutical gel according to claim 1, wherein the amount of flurbiprofen makes up 0.10 to 8% of the total weight of composition and the amount of thiocolchicoside makes up 0.10 to 6% of the total weight of composition.

12. The pharmaceutical gel according to claim 1, wherein the amount of flurbiprofen makes up 0.25 to 6% of the total weight of composition and the amount of thiocolchicoside makes up 0.15 to 5% of the total weight of composition.

* * * * *